United States Patent
Knodel et al.

(10) Patent No.: US 8,505,800 B1
(45) Date of Patent: Aug. 13, 2013

(54) FEEDER BELT FOR TRUE MULTI-FIRE SURGICAL STAPLER

(71) Applicant: Cardica, Inc., Redwood City, CA (US)

(72) Inventors: Bryan D. Knodel, Flagstaff, AZ (US); Philipe R. Manoux, Oakland, CA (US)

(73) Assignee: Cardica, Inc., Redwood City, CA (US)

( * ) Notice: Subject to any disclaimer, the term of this patent is extended or adjusted under 35 U.S.C. 154(b) by 0 days.

(21) Appl. No.: 13/663,424

(22) Filed: Oct. 29, 2012

Related U.S. Application Data

(62) Division of application No. 12/770,462, filed on Apr. 29, 2010, now Pat. No. 8,317,072.

(60) Provisional application No. 61/175,027, filed on May 3, 2009.

(51) Int. Cl.
*A61B 17/068* (2006.01)

(52) U.S. Cl.
USPC ....... 227/175.1; 227/19; 227/176.1; 606/139; 606/219

(58) Field of Classification Search
USPC ............... 227/19, 176.1, 175.1, 180.1, 178.1; 606/139, 151, 153, 219
See application file for complete search history.

(56) References Cited

U.S. PATENT DOCUMENTS

| | | | |
|---|---|---|---|
| 3,581,551 A | 6/1971 | Wilkinson | |
| 3,650,453 A | 3/1972 | Smith, Jr. | |
| 3,675,688 A | 7/1972 | Bryan et al. | |
| 3,899,914 A | 8/1975 | Akiyama | |
| 3,955,581 A | 5/1976 | Spasiano et al. | |
| 4,086,926 A | 5/1978 | Green et al. | |
| 4,127,227 A | 11/1978 | Green | |
| 4,228,895 A | 10/1980 | Larkin | |

(Continued)

FOREIGN PATENT DOCUMENTS

| | | |
|---|---|---|
| EP | 1238634 | 9/1994 |
| EP | 1464287 | 10/2004 |

(Continued)

OTHER PUBLICATIONS

Cardica, Inc., "Cardica Microcutter Implant Delivery Device 510(k), Cover Sheet, Table 10.1, "Substantial Equivalence Comparison," and Section 12, "Substantial Equivalence Discussion"" (Oct. 18, 2010).

(Continued)

*Primary Examiner* — Scott A. Smith
(74) *Attorney, Agent, or Firm* — Cardica, Inc.

(57) ABSTRACT

An exemplary surgical apparatus may include a feeder belt configured as a continuous loop; staples fixed to and shearable from the continuous feeder belt; apertures defined in the continuous feeder belt; and a gear positioned at the distal end of the feeder belt within the continuous loop, where the gear engages at least one of the apertures to move the continuous feeder belt around the gear. Another exemplary surgical apparatus may include a feeder belt; a plurality of staples fixed to and shearable from the continuous feeder belt; and a plurality of teeth defined on the continuous feeder belt. Another exemplary surgical apparatus may include a continuous belt assembly that has a flexible rack with two ends, and a feeder belt with two ends, each end of the feeder belt connected to a corresponding end of the flexible rack; and staples fixed to and shearable from the continuous feeder belt.

8 Claims, 4 Drawing Sheets

(56) References Cited

U.S. PATENT DOCUMENTS

| | | |
|---|---|---|
| 4,275,813 A | 6/1981 | Noiles et al. |
| 4,475,679 A | 10/1984 | Fleury, Jr. |
| 4,589,416 A | 5/1986 | Green |
| 4,633,861 A | 1/1987 | Chow et al. |
| 4,655,222 A | 4/1987 | Florez et al. |
| 4,719,917 A | 1/1988 | Barrows et al. |
| 4,762,260 A | 8/1988 | Richards et al. |
| 4,969,591 A | 11/1990 | Richards et al. |
| 4,978,049 A | 12/1990 | Green |
| 5,156,315 A | 10/1992 | Green et al. |
| 5,170,925 A | 12/1992 | Madden et al. |
| 5,192,288 A | 3/1993 | Thompson et al. |
| 5,269,792 A | 12/1993 | Kovac et al. |
| 5,307,976 A | 5/1994 | Olson et al. |
| 5,413,272 A | 5/1995 | Green et al. |
| 5,476,206 A | 12/1995 | Green |
| 5,547,117 A | 8/1996 | Hamblin et al. |
| 5,553,765 A | 9/1996 | Knodel et al. |
| 5,620,289 A | 4/1997 | Curry |
| 5,630,541 A | 5/1997 | Williamson, IV et al. |
| 5,655,698 A | 8/1997 | Yoon |
| 5,662,260 A | 9/1997 | Yoon |
| 5,692,668 A | 12/1997 | Schulze et al. |
| 5,810,855 A | 9/1998 | Rayburn et al. |
| 5,816,471 A | 10/1998 | Plyley et al. |
| 5,855,311 A | 1/1999 | Hamblin et al. |
| 5,871,135 A | 2/1999 | Williamson, IV et al. |
| 5,875,538 A | 3/1999 | Kish et al. |
| 5,894,979 A | 4/1999 | Powell |
| 5,918,791 A | 7/1999 | Sorrentino et al. |
| 5,964,774 A | 10/1999 | McKean et al. |
| 6,306,149 B1 | 10/2001 | Meade |
| 6,391,038 B2 | 5/2002 | Vargas et al. |
| 6,419,682 B1 | 7/2002 | Appleby et al. |
| 6,592,597 B2 | 7/2003 | Grant et al. |
| 6,602,252 B2 | 8/2003 | Mollenauer |
| 6,716,232 B1 | 4/2004 | Vidal et al. |
| 6,817,508 B1 | 11/2004 | Racenet |
| 6,843,403 B2 | 1/2005 | Whitman |
| 6,994,714 B2 | 2/2006 | Vargas et al. |
| 7,025,747 B2 | 4/2006 | Smith |
| 7,055,730 B2 | 6/2006 | Ehrenfels et al. |
| 7,097,089 B2 | 8/2006 | Marczyk |
| 7,111,768 B2 | 9/2006 | Cummins et al. |
| 7,128,253 B2 | 10/2006 | Mastri et al. |
| 7,140,527 B2 | 11/2006 | Ehrenfels et al. |
| 7,168,604 B2 | 1/2007 | Milliman et al. |
| 7,172,104 B2 | 2/2007 | Scirica et al. |
| 7,179,267 B2 | 2/2007 | Nolan et al. |
| 7,207,471 B2 | 4/2007 | Heinrich et al. |
| 7,213,736 B2 | 5/2007 | Wales et al. |
| 7,225,963 B2 | 6/2007 | Scirica |
| 7,234,624 B2 | 6/2007 | Gresham et al. |
| 7,238,195 B2 | 7/2007 | Viola |
| 7,258,262 B2 | 8/2007 | Mastri et al. |
| 7,401,720 B1 | 7/2008 | Durrani |
| 7,434,715 B2 | 10/2008 | Shelton, IV et al. |
| 7,467,740 B2 | 12/2008 | Shelton, IV et al. |
| 7,497,865 B2 | 3/2009 | Willis et al. |
| 7,506,791 B2 | 3/2009 | Omaits et al. |
| 7,517,356 B2 | 4/2009 | Heinrich |
| 7,588,177 B2 | 9/2009 | Racenet |
| 7,604,151 B2 | 10/2009 | Hess et al. |
| 7,635,073 B2 | 12/2009 | Heinrich |
| 7,635,373 B2 | 12/2009 | Ortiz |
| 7,641,432 B2 | 1/2010 | Lat et al. |
| 7,644,848 B2 | 1/2010 | Swayze et al. |
| 7,918,376 B1 | 4/2011 | Knodel et al. |
| 7,954,683 B1 | 6/2011 | Knodel et al. |
| 7,963,432 B2 | 6/2011 | Knodel et al. |
| 7,988,026 B2 | 8/2011 | Knodel et al. |
| 8,056,789 B1 | 11/2011 | White et al. |
| 8,070,034 B1 | 12/2011 | Knodel |
| 8,096,457 B1 | 1/2012 | Manoux et al. |
| 8,317,072 B1 * | 11/2012 | Knodel et al. ............. 227/175.1 |
| 2003/0120284 A1 | 6/2003 | Palacios et al. |
| 2003/0236551 A1 | 12/2003 | Peterson |
| 2005/0184121 A1 | 8/2005 | Heinrich |
| 2006/0011699 A1 | 1/2006 | Olson et al. |
| 2006/0041273 A1 | 2/2006 | Ortiz et al. |
| 2006/0151567 A1 | 7/2006 | Roy |
| 2006/0253143 A1 | 11/2006 | Edoga |
| 2007/0027472 A1 | 2/2007 | Hiles et al. |
| 2007/0034668 A1 | 2/2007 | Holsten et al. |
| 2007/0073341 A1 | 3/2007 | Smith et al. |
| 2007/0083234 A1 | 4/2007 | Shelton, IV et al. |
| 2007/0118163 A1 | 5/2007 | Boudreaux et al. |
| 2007/0125828 A1 | 6/2007 | Rethy et al. |
| 2007/0175950 A1 | 8/2007 | Shelton, IV et al. |
| 2008/0078807 A1 | 4/2008 | Hess et al. |
| 2008/0272175 A1 | 11/2008 | Holsten et al. |

FOREIGN PATENT DOCUMENTS

| | | |
|---|---|---|
| EP | 1736104 | 3/2009 |
| JP | 2005160933 | 6/2005 |
| RU | 2080833 | 6/1997 |
| WO | WO 8101953 | 7/1981 |
| WO | WO 8501427 | 4/1985 |

OTHER PUBLICATIONS

Gong, Shao W., "Perfectly flexible mechanism and integrated mechanism system design," Mechanism and Machine Theory 39:1155-1174 (Nov. 2004).

Kolios, Efrossini et al., "Microlaparoscopy," J. Endourology 18 (9):811-817 (Nov. 2004).

Lim, Jonas J., et al., "A review of mechanism used in laparascopic surgical instruments," Mechanism and Machine Theory 38:1133-1147 (2003).

Lim, Jonas J., et al., "Application of Type Synthesis Theory to the Redesign of a Complex Surgical Instrument," Journal of Biomechanical Engineering 124:265-272 (Jun. 2004).

Lim, Jyue B., "Type Synthesis of a Complex Surgical Device," Masters Thesis (Feb. 21, 2001).

Steichen, Felicien M., et al., "Mechanical Sutures in Surgery," Brit. J. Surg. 6013.1 (Mar. 1973), 191-197.

Documents from International Application No. PCT/US08/075449, filed Sep. 5, 2008: Notice of Transmittal, International Search Report and Written Opinion mailed Apr. 29, 2009.

\* cited by examiner

FEEDER BELT FOR TRUE MULTI-FIRE SURGICAL STAPLER

CROSS-REFERENCE TO RELATED APPLICATIONS

This application is a divisional of patent application Ser. No. 12/770,462, filed Apr. 29, 2010, now U.S. Pat. No. 8,317,072, which claims priority to Provisional Patent Application No. 61/175,027, filed May 3, 2009, which are hereby incorporated herein by reference in their entireties and from which priority is hereby claimed under 35 U.S.C. §§119 and 120.

FIELD OF THE INVENTION

The invention generally relates to surgical staplers and stapling.

BACKGROUND

An endocutter is a surgical tool that staples and cuts tissue to transect that tissue while leaving the cut ends hemostatic. An endocutter is small enough in diameter for use in minimally invasive surgery, where access to a surgical site is obtained through a trocar, port, or small incision in the body. A linear cutter is a larger version of an endocutter, and is used to transect portions of the gastrointestinal tract. A typical endocutter receives at its distal end a disposable single-use cartridge with several rows of staples, and includes an anvil opposed to the cartridge. During actuation of an endocutter, the cartridge fires all of the staples that it holds. In order to deploy more staples, the endocutter must be moved away from the surgical site and removed from the patient, after which the old cartridge is exchanged for a new cartridge. The endocutter is then reinserted into the patient. However, it can be difficult and/or time-consuming to located the surgical site after reinsertion. Further, the process of removing the endocutter from the patient after each use, replacing the cartridge, and then finding the surgical site again is tedious, inconvenient and time-consuming, particularly where a surgical procedure requires multiple uses of the endocutter.

In order to overcome these difficulties, Cardica, Inc. of Redwood City, Calif. has developed a true multi-fire endocutter that is capable of firing multiple times without the need to utilize single-use-cartridges. That endocutter is described in, for example, application Ser. No. 12/263,171, filed Oct. 31, 2008 (the "Endocutter Application"), which is hereby incorporated herein by reference in its entirety. Referring to FIG. 1, the Endocutter Application, among other items, discloses a feeder belt 2 to which a plurality of staples 4 are frangibly attached. The feeder belt 2 bends around a pulley 6 at its distal end. Each end of the feeder belt 2 is connected to a different rigid, toothed rack 8, and each rack engages a gear 10. The racks 8 are rigid, and as a result advancement of one rack 8 causes the gear 10 to rotate and thereby move the other rack 8 in the opposite direction. The gear 10 is located in a shaft 12 of the tool, between the handle and a distal end of the shaft. Because the racks 8 are rigid, the linear travel of the racks 8 is limited by the length of the shaft 12 and of the handle connected to the shaft. Consequently, the number of firings that can be made by the tool is limited by the linear distance that the racks 8 can travel within the shaft 12 and structure connected to the shaft 12.

BRIEF DESCRIPTION OF THE DRAWINGS

The use of the same reference symbols in different figures indicates similar or identical items.

DETAILED DESCRIPTION

Continuous Feeder Belt Assembly with Flexible Rack

Figure 1:
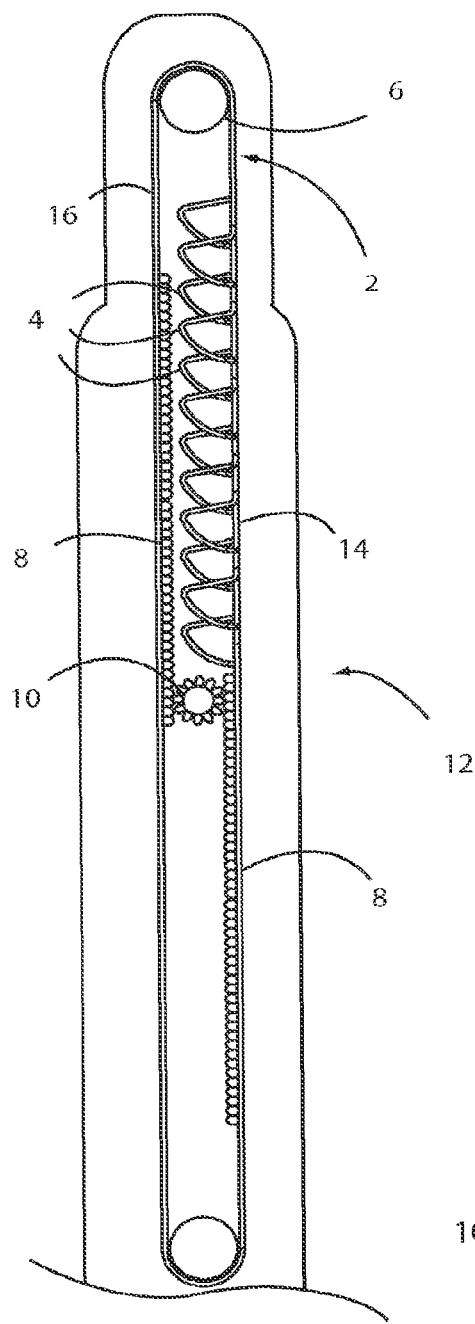
FIG. 1 is a schematic view of an endocutter utilizing a feeder belt connected at each end to a different rigid rack.
Figure 2:
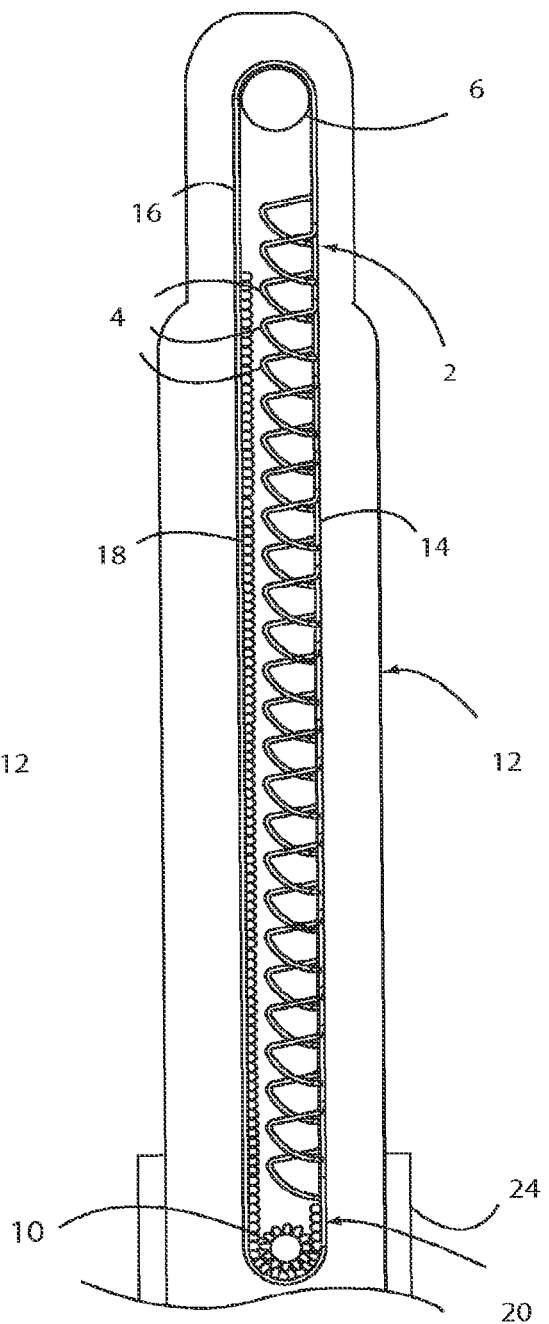
FIG. 2 is a schematic view of an endocutter utilizing a feeder belt connected at each end to a single flexible rack.

Referring to FIG. 2, a feeder belt 2 bends around a pulley 6 at its distal end, such that an upper portion 14 of the feeder belt 2 is above and spaced apart from a lower portion 16 of the feeder belt 2. The upper portion 14 and lower portion 16 of the feeder belt 2 may be, but need not be, substantially parallel to one another. The upper portion 14 and lower portion 16 of the feeder belt 2 each have a proximal end, and the proximal end of each portion 14, 16 may be connected to a flexible rack 18. That is, the feeder belt 2 is connected at each end to a flexible rack 18. The combination of the feeder belt 2 and the flexible rack 18 may be referred to as the belt assembly 20. The belt assembly 20 is continuous, meaning that the belt assembly 20 defines a continuous, unbroken loop. The flexible rack 18 may be flexible in any suitable manner. As one example, the flexible rack 18 may be made from a flexible material with sufficient strength and other material properties to allow it to bend around the gear 10, and to be attached to and exert tension on the feeder belt 2. As another example, the flexible rack 18 may be a chain or other mechanism with individual, small links that are themselves rigid but that are collectively flexible. As another example, the flexible rack 18 may be fabricated from nickel-titanium alloy or other superelastic material.

Where the flexible rack 18 is utilized, the gear 10 may be located at the proximal end of the continuous belt assembly 20. In this way, the gear 10 may be utilized to tension the feeder belt 2 between the gear 10 and the pulley 6 at the distal end of the feeder belt 2. If so, the gear 10 may be located at or near the proximal end of the shaft 12, which may be held within a handle 24, or may be located proximal to or outside the shaft 12 inside the handle 24 or other structure attached to the shaft 12. Further, the initial position of the feeder belt 2 may be as shown in FIG. 2, where staples 4 extend from the upper portion 14 of the feeder belt 2 along substantially all of the upper portion 14. In this way, the feeder belt 2 is able to include more staples 4 along its length than the feeder belt 2 of FIG. 1, such that more staple firings can be made with a single feeder belt 2.

The feeder belt 2 may be assembled into an endocutter or other surgical apparatus, and may be actuated by that endocutter or other surgical apparatus, substantially as described in the Endocutter Application. Optionally, the gear 10 may be directly driven by a handle such as described in the Endocutter Application, thereby reducing the number of parts and simplifying the overall assembly relative to that handle.

Figure 3:
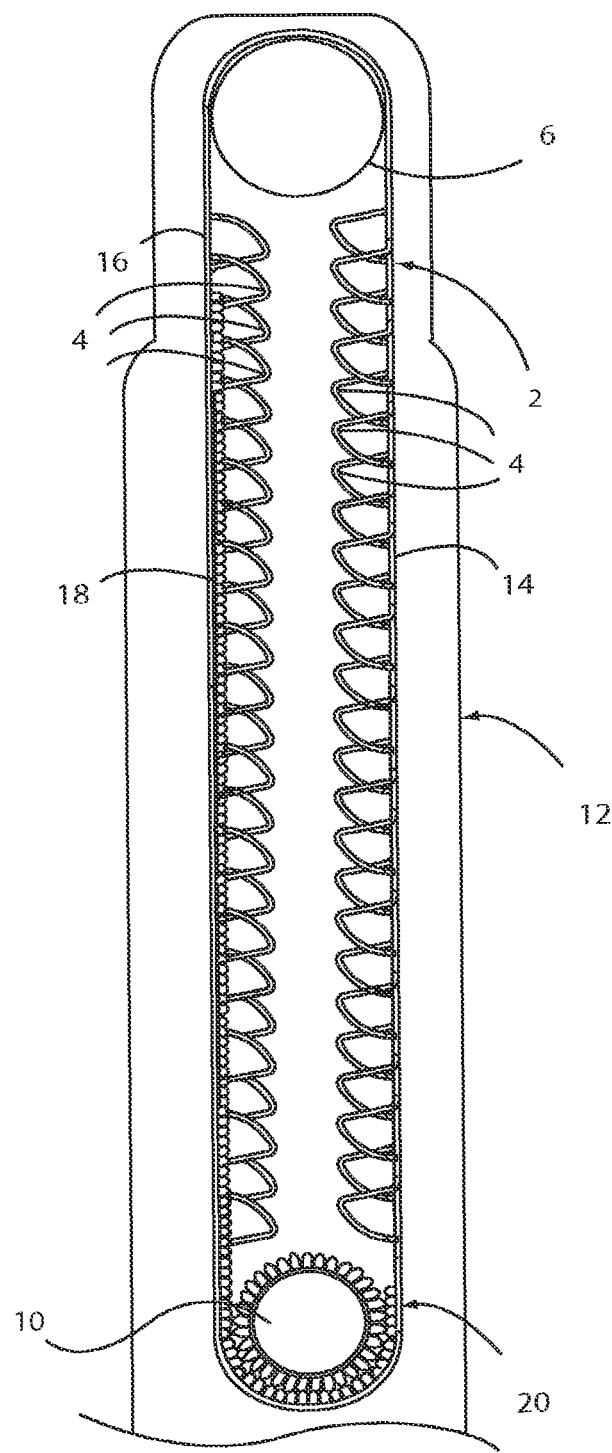
FIG. 3 is a schematic view of an endocutter utilizing a feeder belt connected at each end to a single flexible rack, where staples extend from the flexible rack.

Optionally, referring also to FIG. 3, staples 4 may be frangibly connected to the flexible rack 18 as well as to the feeder belt 2. The staples 4 may be connected to the flexible rack 18 in substantially the same manner as described in the Endocutter Application. Alternately, the staples 4 may be connected to the flexible rack 18 in any other suitable manner. Where staples 4 are carried by the flexible rack 18, the upper portion 14 of the feeder belt 2 may be spaced apart from the lower portion 16 of the feeder belt 2 a distance sufficient that the staples 4 extending from each portion 14, 16 do not interfere with or engage one another. Alternately, the staples 4 instead, or also, may be laterally spaced relative to one another, such that in the initial position of the feeder belt 2, the staples 4 extending from the upper portion 14 of the continuous belt assembly 20 are laterally spaced a first distance from a longitudinal centerline of that continuous belt assembly 20, and the staples 4 extending from the lower portion 16 of the continuous belt assembly 20 are laterally spaced a second distance from a longitudinal centerline of that continuous belt assembly 20, where the first distance and the second distance are sufficiently different from one another that the staples 4 extending from different portions 14, 16 pass by one another without colliding or interfering with one another during actuating of the continuous belt assembly 20. That is, the continuous belt assembly 20 is arranged in any suitable manner such that the staples 4 along the feeder belt 2 and the flexible rack 18 of the continuous belt assembly 20 do not interfere with one another.

Alternately, where staples 4 extend from the flexible rack 18, the feeder belt 2 may be omitted, such that the flexible rack 18 is continuous and holds and deploys all of the staples 4.

Rackless Continuous Feeder Belt Assembly

Figure 4:
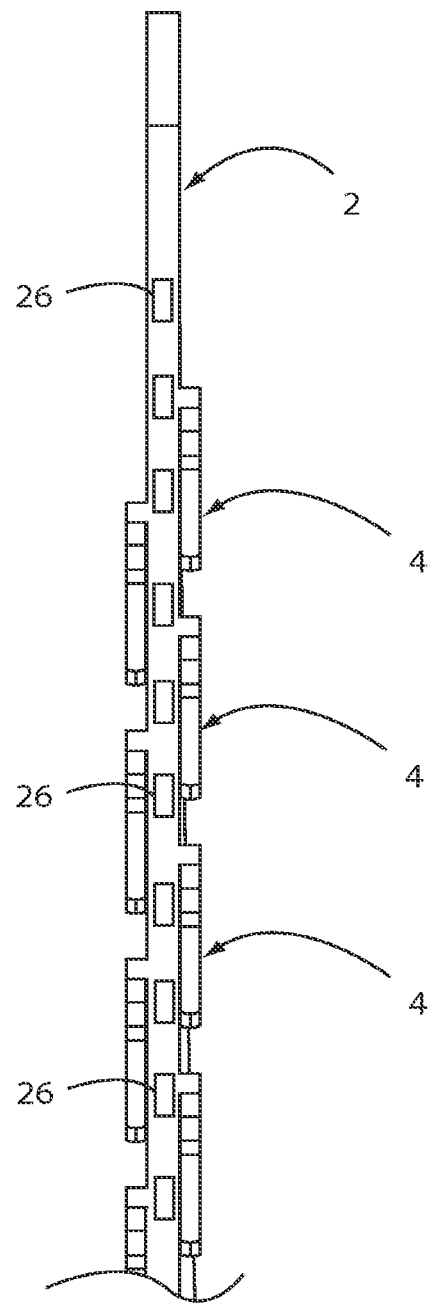
FIG. 4 is a top view of an exemplary feeder belt configured to engage a gear.
Figure 5:
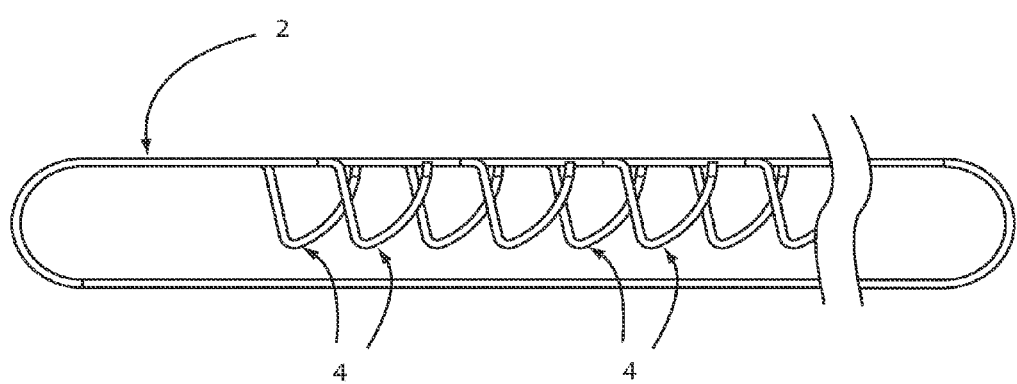
FIG. 5 is a side view of an exemplary continuous feeder belt.

Referring to FIG. 4, a feeder belt 2 such as described in the Endocutter Application may include a plurality of apertures 26 defined therein. The apertures 26 may be sized, shaped and spaced apart from one another such that they engage teeth on the gear 10. The feeder belt 2 is sufficiently flexible to wrap around and be driven around the pulley 6, and consequently is sufficiently flexible to wrap around and be driven by or around the gear 10. In such an embodiment, the rack or racks 8, 18 may be omitted, and the feeder belt 2 is itself continuous and forms a continuous loop, as shown in FIG. 5. Alternately, the apertures 26 may be omitted, and the underside of the feeder belt 2 may include teeth similar to one of the racks 8, 18 configured to engage the gear 10. Alternately, the apertures 26 may be omitted, and the feeder belt 2 may be held in tension or otherwise manipulated such that the flat feeder belt 2 is capable of being advanced without the use of features on the feeder belt 2 configured to engage a gear, or without the use of a rack 8, 18 connected to or otherwise engaging the feeder belt 2.

What is claimed is:

1. A surgical apparatus, comprising:
a feeder belt configured as a continuous loop;
staples fixed to and shearable from said continuous feeder belt;
apertures defined in said continuous feeder belt; and
a gear positioned at the distal end of said feeder belt within said continuous loop, wherein said gear engages at least one of said apertures to move said continuous feeder belt around said gear.

2. The surgical apparatus of claim 1, wherein at least one said aperture is defined completely through said continuous feeder belt.

3. The surgical apparatus of claim 1, wherein said gear includes a plurality of teeth.

4. The surgical apparatus of claim 1, wherein said staples are arranged along substantially the entire length of said feeder belt.

5. The surgical apparatus of claim 1, wherein at least one said aperture is substantially rectangular.

6. A surgical apparatus, comprising:
a feeder belt;
a plurality of staples fixed to and shearable from said continuous feeder belt; and
a plurality of teeth defined on said continuous feeder belt.

7. The surgical apparatus of claim 6, wherein said feeder belt is a continuous loop.

8. The surgical apparatus of claim 6, further comprising at least one gear having at least one gear tooth; wherein at least one said tooth defined on said gear engages at least one said tooth defined on said continuous feeder belt to drive said continuous feeder belt around said gear.

* * * * *